(12) United States Patent
Lee et al.

(10) Patent No.: US 6,716,615 B2
(45) Date of Patent: Apr. 6, 2004

(54) STRAINS OF SACCHARAOTHRIX, PROCESS FOR PRODUCING PRAVASTATIN USING THE STRAINS AND ISOLATION PROCESS OF (HMG)-COA REDUCTASE

(75) Inventors: Fang-Yu Lee, Taichung (TW); Ming-Liang Lee, Taichung (TW); Anderson C. Hong, Taipei (TW)

(73) Assignee: Yung Shin Pharmaceutical Ind. Co., Ltd. (CN)

( * ) Notice: Subject to any disclaimer, the term of this patent is extended or adjusted under 35 U.S.C. 154(b) by 0 days.

(21) Appl. No.: 10/085,871

(22) Filed: Feb. 27, 2002

(65) Prior Publication Data

US 2003/0199047 A1 Oct. 23, 2003

(51) Int. Cl.$^7$ .............................. C12P 17/06; C12N 1/20
(52) U.S. Cl. ..................................... 435/252.1; 435/125
(58) Field of Search ............................... 435/252.1, 125

(56) References Cited

FOREIGN PATENT DOCUMENTS

WO          WO0110813          2/2001

*Primary Examiner*—Herbert J. Lilling
(74) *Attorney, Agent, or Firm*—Blakely, Sokoloff, Taylor & Zafman

(57) ABSTRACT

The present invention provides two new microorganism strains of Saccharothrix, designated as YS-44442 and YS-45494, a process of producing pravastatin using the strains, and an improved process for isolation of (HMG)-CoA reductase inhibitors.

12 Claims, 1 Drawing Sheet

SEQUENCE LISTING

<160> NUMBER OF SEQ ID NOS: 12

<210> SEQ ID NO 1
<211> LENGTH: 1437
<212> TYPE: DNA
<213> ORGANISM: Saccharothrix 44442

<400> SEQUENCE: 1

| | | | | | |
|---|---|---|---|---|---|
| gacgaacgct | ggcggcgtgc | ttaacacatg | caagtcgagc | ggtaaggccc | ttcggggtac | 60 |
| acgagcggcg | aacgggtgag | taacacgtgg | gtaacctgcc | ctgtactccg | ggataagcct | 120 |
| gggaaactag | gtctaatacc | ggatacgacc | ccatagggca | tcttgtgggg | tggaaagttc | 180 |
| cggcggtatg | ggatggaccc | gcggcctatc | agcttgttgg | tgggtgatg | gcctaccaag | 240 |
| gcgacgacgg | gtagccggcc | tgagagggtg | accggccaca | ctgggactga | gacacggccc | 300 |
| agactcctac | gggaggcagc | agtggggaat | attgcacaat | gggcgaaagc | ctgatgcagc | 360 |
| gacgccgcgt | gagggatgac | ggccttcggg | ttgtaaacct | ctttcagcag | ggacgaagcg | 420 |
| caagtgacgg | tacctgcaga | agaagcaccg | gctaactacg | tgccagcagc | cgcggtaata | 480 |
| cgtagggtgc | gagcgttgtc | cggaattatt | gggcgtaaag | agctcgtagg | cggtttgttg | 540 |
| cgtcggccgt | gaaaacttca | cgcttaacgt | ggagcctgcg | gtcgatacgg | gcagacttga | 600 |
| gttcggcagg | ggagactgga | attcctggtg | tagcggtgaa | atgcgcagat | atcaggagga | 660 |
| acaccggtgg | cgaaggcggg | tctctgggcc | gatactgacg | ctgaggagcg | aaagcgtggg | 720 |
| gagcgaacag | gattagatac | cctggtagtc | cacgccgtaa | acgttgggtg | ctaggtgtgg | 780 |
| gggacttcca | cgtcctccgt | gccgcagcta | acgcattaag | cacccgcct | ggggagtacg | 840 |
| gccgcaaggc | taaaactcaa | aggaattgac | gggggcccgc | acaagcggcg | gagcatgtgg | 900 |
| attaattcga | tgcaacgcga | agaaccttac | ctgggcttga | catgcaccgg | aaacctgcag | 960 |
| agatgtaggc | ctcttcggac | tggtgtacag | gtggtgcatg | gctgtcgtca | gctcgtgtcg | 1020 |
| tgagatgttg | ggttaagtcc | cgcaacgagc | gcaaccctcg | ttccatgttg | ccagcgcgtt | 1080 |
| atggcgggga | ctcatgggag | actgccgggg | tcaactcgga | ggaaggtggg | gatgacgtca | 1140 |
| agtcatcatg | cccttatgt | ccagggcttc | acacatgcta | caatggccgg | tacagagggc | 1200 |
| tgctaagccg | tgaggtggag | cgaatcccaa | aaagccggtc | tcagttcgga | tcgggtctg | 1260 |
| caactcgacc | ccgtgaagtc | ggagtcgcta | gtaatcgcag | atcagcaacg | ctgcggtgaa | 1320 |
| tacgttcccg | ggccttgtac | acaccgcccg | tcacgtcacg | aaagtcggta | acacccgaag | 1380 |
| cccgtggccc | aacccgcaag | gggggagcg | gtcgaaggtg | ggactggcga | ttgggac | 1437 |

<210> SEQ ID NO 2
<211> LENGTH: 1471
<212> TYPE: DNA
<213> ORGANISM: Saccharothrix 45494

<400> SEQUENCE: 2

| | | | | | |
|---|---|---|---|---|---|
| gacgaacgct | ggcggcgtgc | ttaacacatg | caagtcgagc | ggtaaggccc | ttcggggtac | 60 |
| acgagcggcg | aacgggtgag | taacacgtgg | gtaacctgcc | ctgtactccg | ggataagcct | 120 |
| gggaaactag | gtctaatacc | ggatacgacc | ccataaggca | tcttgtgggg | tggaaagttc | 180 |
| cggcggtatg | ggatggaccc | gcggcctatc | agcttgttgg | tgggtgatg | gcctaccaag | 240 |
| gcgacgacgg | gtagccggcc | tgagagggtg | accggccaca | ctgggactga | gacacggccc | 300 |
| agactcctac | gggaggcagc | agtggggaat | attgcacaat | gggcgaaagc | ctgatgcagc | 360 |

```
gacgccgcgt gagggatgac ggccttcggg ttgtaaacct ctttcagcag ggacgaagcg    420
caagtgacgg tacctgcaga agaagcaccg gctaactacg tgccagcagc cgcggtaata    480
cgtagggtgc gagcgttgtc cggaattatt gggcgtaaag agctcgtagg cggtttgttg    540
cgtcggccgt gaaaacttca cgcttaacgt ggagcctgcg gtcgatacgg gcagacttga    600
gttcggcagg ggagactgga attcctggtg tagcggtgaa atgcgcagat atcaggagga    660
acaccggtgg cgaaggcggg tctctgggcc gatactgacg ctgaggagcg aaagcgtggg    720
gagcgaacag gattagatac cctggtagtc cacgccgtaa acgttgggtg ctaggtgtgg    780
gggacttcca cgtcctccgt gccgcagcta acgcattaag caccccgcct ggggagtacg    840
gccgcaaggc taaaactcaa aggaattgac ggggcccgc acaagcggcg gagcatgtgg     900
attaattcga tgcaacgcga agaaccttac ctgggcttga catgcaccgg aaacctgcag    960
agatgtaggc ctcttcggac tggtgtacag gtggtgcatg gctgtcgtca gctcgtgtcg    1020
tgagatgttg ggttaagtcc cgcaacgagc gcaaccctcg ttccatgttg ccagcgcgtt    1080
atggcgggga ctcatgggag actgccgggg tcaactcgga ggaaggtggg gatgacgtca    1140
agtcatcatg ccccttatgt ccagggcttc acacatgcta caatggccgg tacagagggc    1200
tgctaagccg tgaggtggag cgaatcccaa aaagccggtc tcagttcgga tcggggtctg    1260
caactcgacc ccgtgaagtc ggagtcgcta gtaatcgcag atcagcaacg ctgcggtgaa    1320
tacgttcccg ggccttgtac acaccgcccg tcacgtcacg aaagtcggta acacccgaag    1380
cccgtggccc aacccgcaag gggggagcg gtcgaaggtg ggactggcga ttgggacgaa    1440
gtcgtaacaa ggtagccgta ccggaaggtg c                                   1471

<210> SEQ ID NO 3
<211> LENGTH: 19
<212> TYPE: DNA
<213> ORGANISM: Artificial Sequence
<220> FEATURE:
<223> OTHER INFORMATION: Primer of 16s rDNA of Saccharothrix 44442 and
      Saccharothrix 45494

<400> SEQUENCE: 3
gagtttgatc ctggctcag                                                   19

<210> SEQ ID NO 4
<211> LENGTH: 17
<212> TYPE: DNA
<213> ORGANISM: Artificial Sequence
<220> FEATURE:
<223> OTHER INFORMATION: Primer of 16s rDNA of Saccharothrix 44442 and
      Saccharothrix 45494

<400> SEQUENCE: 4
cggtgtgtrc aaggccc                                                     17

<210> SEQ ID NO 5
<211> LENGTH: 16
<212> TYPE: DNA
<213> ORGANISM: Artificial Sequence
<220> FEATURE:
<223> OTHER INFORMATION: Primer of 16s rDNA of Saccharothrix 44442 and
      Saccharothrix 45494

<400> SEQUENCE: 5
gcaacgagcg caaccc                                                      16
```

```
<210> SEQ ID NO 6
<211> LENGTH: 20
<212> TYPE: DNA
<213> ORGANISM: Artificial Sequence
<220> FEATURE:
<223> OTHER INFORMATION: Primer of 16s rDNA of Saccharothrix 44442 and
      Saccharothrix 45494

<400> SEQUENCE: 6
ccgtcaattc atttgagttt                                                   20

<210> SEQ ID NO 7
<211> LENGTH: 17
<212> TYPE: DNA
<213> ORGANISM: Artificial Sequence
<220> FEATURE:
<223> OTHER INFORMATION: Primer of 16s rDNA of Saccharothrix 44442 and
      Saccharothrix 45494

<400> SEQUENCE: 7
attagatacc ctggtag                                                      17

<210> SEQ ID NO 8
<211> LENGTH: 20
<212> TYPE: DNA
<213> ORGANISM: Artificial Sequence
<220> FEATURE:
<223> OTHER INFORMATION: Primer of 16s rDNA of Saccharothrix 44442 and
      Saccharothrix 45494

<400> SEQUENCE: 8
agaaaggagg tgatccagcc                                                   20

<210> SEQ ID NO 9
<211> LENGTH: 18
<212> TYPE: DNA
<213> ORGANISM: Artificial Sequence
<220> FEATURE:
<223> OTHER INFORMATION: Primer of 16s rDNA of Saccharothrix 44442 and
      Saccharothrix 45494

<400> SEQUENCE: 9
gwattaccgc ggckgctg                                                     18

<210> SEQ ID NO 10
<211> LENGTH: 15
<212> TYPE: DNA
<213> ORGANISM: Artificial Sequence
<220> FEATURE:
<223> OTHER INFORMATION: Primer of 16s rDNA of Saccharothrix 44442 and
      Saccharothrix 45494

<400> SEQUENCE: 10
tacgggaggc agcag                                                        15

<210> SEQ ID NO 11
<211> LENGTH: 15
<212> TYPE: DNA
<213> ORGANISM: Artificial Sequence
<220> FEATURE:
<223> OTHER INFORMATION: Primer of 16s rDNA of Saccharothrix 44442 and
      Saccharothrix 45494

<400> SEQUENCE: 11
ctgctgcctc ccgta                                                        15

<210> SEQ ID NO 12
```

-continued

```
<211> LENGTH: 20
<212> TYPE: DNA
<213> ORGANISM: Artificial Sequence
<220> FEATURE:
<223> OTHER INFORMATION: Primer of 16s rDNA of Saccharothrix 44442 and
      Saccharothrix 45494

<400> SEQUENCE: 12
agaaaggagg tgatccagcc                                              20
```

STRAINS OF SACCHARAOTHRIX, PROCESS FOR PRODUCING PRAVASTATIN USING THE STRAINS AND ISOLATION PROCESS OF (HMG)-COA REDUCTASE

FIELD OF THE INVENTION

The present invention relates to two new microorganism strains of Saccharothrix, designated as YS-44442 and YS-45494, a process of producing pravastatin using the strains, and an improved process for isolation of (HMG)-CoA reductase inhibitors.

BACKGROUND OF THE INVENTION

It has been recognized that an elevated blood cholesterol level is one of the major risk factors to atherosclerotic diseases, specifically to coronary heart diseases. The monitor for the cholesterol biosynthesis is very helpful to control the diseases. 3-hydroxy-3-methylglutaryl (HMG)-CoA reductase is the rate-limiting enzyme in the cholesterol biosynthesis. By inhibiting the activity of (HMG)-CoA reductase, blood cholesterol levels in the bodies can be effectively reduced.

A number of (HMG)-CoA reductase inhibitors have been discovered, such as pravastatin, compactin, lovastatin. They have the following formula in the lactone form and may exist in other forms such as the acid form or and the salts and esters thereof.

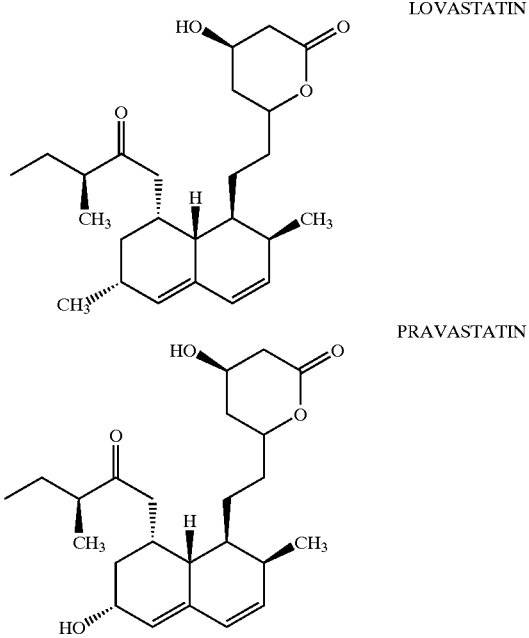

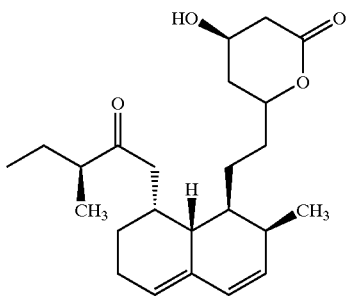

These (HMG)-CoA reductase inhibitors are very effective in lowering blood cholesterol level in most animals including human. Pravastatin is even more active than compactin and lovastatin, and has been applied in the treatment of hypercholesterolemia (Nara, F et al. *Curr. Genet.* 23: 28–32 (1993)).

Pravastatin is a 3 β-hydroxy derivative of compactin. It has been reported that pravastatin is produced by converting compactin through microbial hydroxylation using various genera of fungi and bacteria, such as *Streptomyces roseochrornogenus* (U.S. Pat. No. 4,346,277) and *Actinomadura* sp. (Peng, M. et al., *J. Antibiotics*, December: 1032–1035 (1997), and Peng Y. and A. L. Demain, *J. Mol. Cataly. B: Enzymatic* 10: 151–156 (2000)). However, these fungi or bacteria do not tolerate a high amount of compactin added in the fungal or bacterial fermentation broth, likely due to the anti-fungal activity of compactin, and thus exhibit low productivity of pravastatin. Therefore, there is a need to find a new microorganism which is tolerable to a higher amount of compactin and has effective conversion activity.

In general, the isolation of (HMG)-CoA reductase inhibitors from a fermentation broth is conducted by serious procedures of extraction, chromatography, lactonization and crystallization process. EP 0 877 089A1 discloses a (HMG)-CoA reductase inhibitor preparation process, wherein a fermentation broth containing the inhibitor (e.g., lovastatin) is basified prior to filtration to remove the cells and then the filtrate was loaded through a column. The eluate was extracted with toluene and subsequently the lactonization is conducted to produce the inhibitor.

When using chromatography, however, a large column and a great volume of fermentation broth containing (HMG)-CoA reductase inhibitors are usually needed to obtain a desired yield of the inhibitors, thereby increasing the difficulty in handling the purification process of the inhibitors. Furthermore, a lactonization reaction usually needs much energy and time. Therefore, there is a need to seek an improved process of obtaining a (HMG)-CoA reductase inhibitor in a good yield and purity without proceeding a lactonization reaction and using a chromatography, and so as to reduce the cost.

SUMMARY OF THE INVENTION

One object of the invention is to provide two new microorganism strains of Saccharothrix capable of producing pravastatin designated as YS-44442 and YS-45494 as well as their mutants.

Another object of the invention is to provide a process of producing pravastatin by using the microorganisms of the invention. In particular, the process of producing pravastatin comprises the steps of (a) cultivating YS-44442 or YS-45494 at a suitable condition to generate a fermentation broth; (b) feeding compactin into the broth; (c) fermenting the broth for a period of time to convert the compactin to pravastatin; (d) isolating the pravastatin from the broth.

Still another object of the invention is to provide a process of isolating a (HMG)-CoA reductase inhibitor comprising the steps of (1) adding an ammonium sulfate into a first solution containing the (HMG)-CoA reductase inhibitor to produce a precipitation; (2) isolating the precipitation; (3) dissolving the precipitation with a polar solvent to produce a second solution; (4) adjusting the pH of the second solution to about 4 to about 6; and (5) extracting the second solution with an water immiscible solvent to isolate the (HMG)-CoA reductase inhibitor. The preparation process further comprises a step of reacting the isolated (HMG)-CoA reductase inhibitor with an organic or inorganic cation source to generate a salt form of the inhibitor.

DETAILED DESCRIPTION OF THE INVENTION

Figure 1:
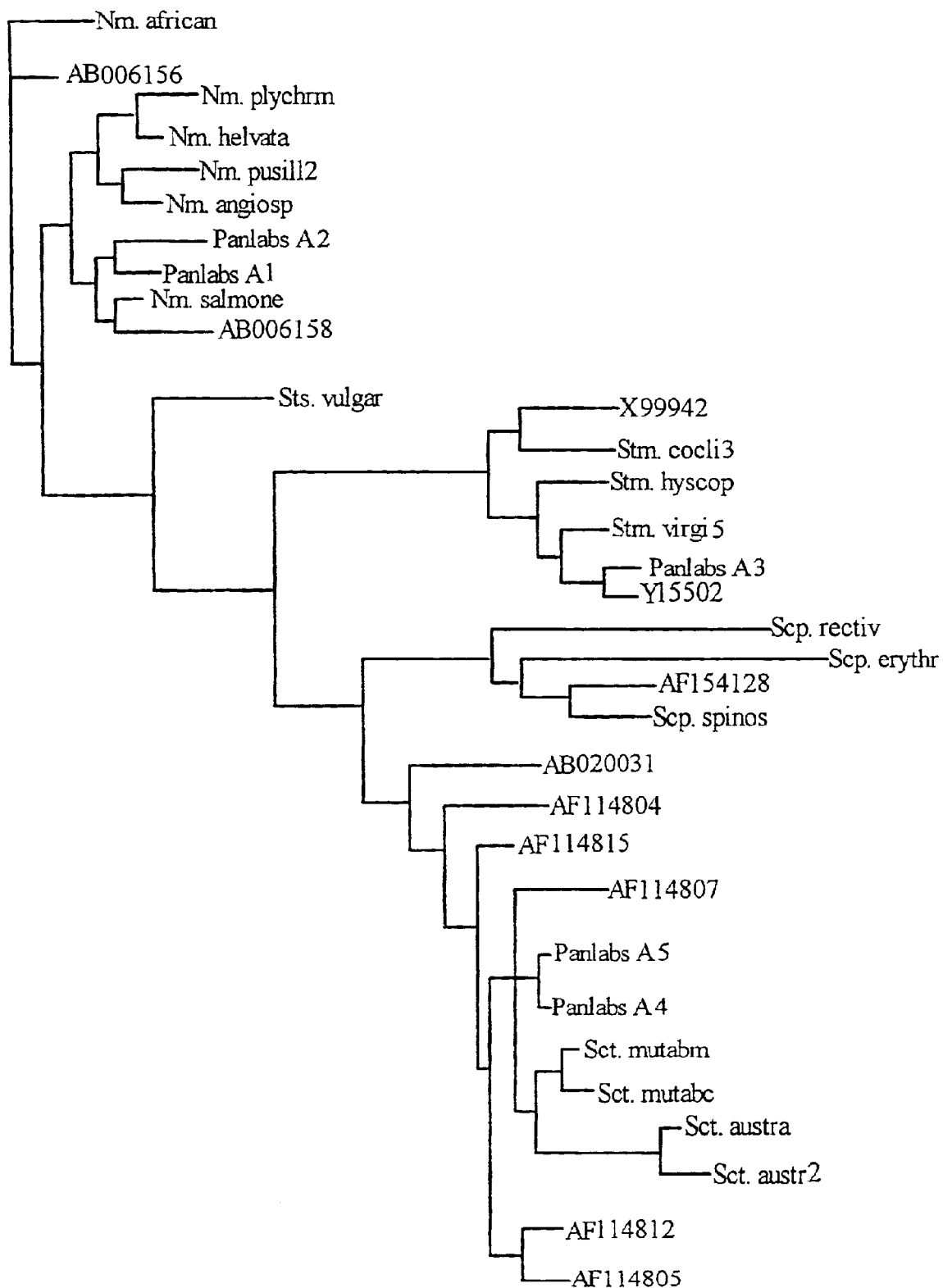
FIG. 1 is a 16s rDNA phylogenetic distance tree comparing YS-44442 and YS-45494 of the invention with related actinomycetes generated with the ARB software package (denoted as Tree 0.1 version).

The present invention will be more fully understood and further advantages will become apparent when reference is made to the following description of the invention.

I. New Microorganism Strains

One object of the invention is to provide two new microorganism strains for producing pravastatin in a good yield. The inventors surprisingly obtained two novel microorganism strains, YS-44442 and YS-45494, through the isolation of actinomycetes from soil samples, showing a high tolerance to compactin and a high productivity of pravastatin. The two strains were deposited with the China Center for Type Culture Collection (CCTCC) under the accession number of M202002 and M202002, respectively, on Jan. 7, 2002.

YS-44442 and YS-45494 can be isolated from soils. A soil sample is suspended in a sterile phosphate buffer and spread, after a 10-fold serial dilution, on an agar plate containing an isolation medium. The colonies growing on the plates can be preliminarily screened based on the morphological characteristics of actinomycetes under a microscopy examination. A candidate strain is then cultivated to give a fermentation broth and fed with compactin to produce pravastatin. The amount of pravastatin thus produced in the broth is determined. Then, YS-44442 and YS-45494 are selected for their high productivities of pravastatin.

The medium of the agar plate is well known in this art, preferably containing yeast extract, malt extract, dextrose and agar, and more preferably ISP 2 medium. In certain embodiments, the isolation reagent contained in the medium preferably contains antibiotics which can be selected from nystatin, cycloheximide, penicillin G, polymyxin B and gentamycin. The morphological characteristics of the genus, Actinomycetes, have been well described in conventional literatures or text books, such as Bergey's Manual of Systematic Bacteriology [Cross, T., *Bergey's Manual of Systematic Bacteriology*, S. T. Williams, Sharpe, M. E., Holt, J. G., Editor (1989) Williams & Wilkins: Baltimore. p. 2586–2615]. In addition, the technologies of cultivation or fermentation of such microorganisms are well known in the art.

The compactin to be fed into a broth is preferably provided by a microorganism (e.g., fungus or bacterium) producing compactin or the cell extract thereof, or a solution comprising compactin. The concentration of compactin fed into a broth is calculated based on the broth without microbe and only the feeding compactin. Pravastatin produced in a fermentation broth can be identified by conventional technologies, such as HPLC, and the amount of pravastatin can be determined by the retention time in comparison with a standard preparation. For example, the yield of pravastatin produced can be determined by Formula (I). In addition, the conversion efficiency of compactin to pravastatin can be calculated by Formula (II) and the epi-pravastatin ratio(Epi %) of the total pravastatin produced is calculated by the formula (III).

$$\text{Pravastatin yield} = (\text{standard concentration/standard Area})*\text{sample area} \tag{I}$$

$$\text{Molar conversion efficiency(ME \%)} = (\text{Number of moles of pravastatin produced/Number of moles of compactin converted})*100 \tag{II}$$

$$\text{Epi-pravastatin ratio(Epi \%)} = (\text{amount of Epi-pravastatin produced/(amount of Epi-pravastatin produced+amount of pravastatin produced}))*100\% \tag{III}$$

Epi-pravastatin is a 6α-hydroxylation form of compactin which does not have a desired therapeutic efficacy and even has a negative effect in clinical therapies. Therefore, a low epi-pravastatin ratio is preferred. In addition, the term "compactin tolerance" used herein means a final concentration of compactin fed into a microbial fermentation broth wherein the concentration is accepted by the microorganism, i.e., the microorganism can normally grow in a medium containing such amount of compactin.

The YS-44442 obtained as described above has the following properties: the colonies (7 days) on plates are pale white without sporulation; the culture in SCY agar slant are pale white with few spores; the conversion efficiency of compactin to pravastatin (ME %) is about 70 to 75%; the epi-pravastatin ratio is 6.5 to 8%; the production of pravastatin is 1.0 to 1.5 g/L by volume of the fermentation broth; and the compactin tolerance is 1.5 to 2.0 g/L. More detailed characteristics of YS-44442 are described in the following examples.

The YS-45494 obtained as described above has the following properties: the colonies (7 days) on plates are white with sporulation; the culture in SCY agar slant produces white spores and yellow pigments; the conversion efficiency of compactin to pravastatin (ME %) is about 48 to 50%; the epi-pravastatin ratio is 1.8 to 3.0%; the production of pravastatin is 1.0 to 1.5 g/L by volume of the fermentation broth; and the compactin tolerance reaches 1.5 to 2.0 g/L. More detailed characteristics of YS-45494 are described in the following examples.

Mutants derived from YS-44442 and YS-45494 capable of producing pravastafin are also included in the invention. The mutants can be obtained by applying a conventional mutation-inducing technique to the parent YS-44442 and YS-45494. For example, irradiation of the microorganisms with gamma rays or ultraviolet light, or treated with a mutagen, such as EMS (ethylmethane sulfonate), NTG (N-methyl-N-nitro-N'-nitrosoguanidine, NQO (4-nitroquinoline N-oxide), DES (diethylsulfate), DEB (diepoxybutane) and NMU (N-methyl-N-nitrosourea) are suitable methods of inducing mutation. To obtain a mutant, the parent strain YS-44442 and YS-45494 may be treated with UV irradiation for 30, 60, 120, 240 or 480 seconds, or with cobalt 60 gamma irradiation in an amount of 0.5, 1, 2, 3 or 4 Kgy. A desirable mutant strain capable of producing pravastatin in good yield can be selected by the method as described above. Persons skilled in the art can obtain such mutants from the parent YS-44442 and YS-45494 according to the mutagenesis technologies and screening method conventional to the art. More detailed procedures of the mutagenesis procedures are described in the following examples.

II. Process for Producing Pravastatin Using the Strains of the Invention

YS-44442 and YS-45494 can be used to produce pravastatin. Accordingly, one object of the invention is to provide a process of producing pravastatin of using YS-44442 and YS-45494. In particular, the process comprises the steps of (a) cultivating YS-44442 or YS-45494 in a suitable condition to generate a fermentation broth; (b) feeding compactin into the broth; (c) fermenting the broth for a period of time to convert the compactin to the pravastatin; (d) isolating the pravastatin from the broth.

The technologies of cultivating such microorganisms and those of isolating pravastatin from a fermentation broth are well known in the art. Persons skilled in the art can accomplish the production process of pravastatin using YS-44442 and YS-45494 of the invention in combination with any fermentation and isolation technologies (e.g., HPLC) known in the art. A particular example is illustrated later.

In one embodiment of the invention, the fermentation broth of Step (a) is incubated for less than 2 days and preferably for about 18 hours. The fermentation broth of Step (a) is preferably derived from a seed culture of the microorganism which is cultivated under a suitable condition for about 18 to 48 hrs. A seed medium for cultivating the seed culture can contain glucose, peptone, soy protein and mineral sources. A fermentation medium can further contain corn steep powder (C.S.P.).

The compactin to be added in the broth is preferably provided by a fungus or bacterium capable of producing compactin or the cell extract thereof, or a solution comprising compactin. The concentration of compactin fed in a broth is calculated based on the broth without microbe and only the feeding compactin. In a preferred embodiment of the invention, the compactin is fed into the broth in a final concentration of higher than 1.0 g/L and more preferably in a range of 1.5 to 2.0 g/L.

In another embodiment of the invention, the period of time of Step (c) to convert the compactin to the pravastatin is less than 5 days, preferably less than 3 days and more preferably less than 24 hours.

In one preferred embodiment of the invention, the pravastatin isolated from Step (d) yields more than 0.5 g/L, preferably more than 1.0 g/L and most preferably about 1.5 g/L. In one preferred embodiment of the invention, the epi-pravastatin ratio (EP %) of the total pravastatin produced from Step (d) is about 1.8 to 8%. In one preferred embodiment of the invention, the conversion efficiency (ME %) of compactin to pravastatin is higher than 40%, more preferably higher than 50%, still more preferably higher than 70%. The pravastatin produced form the above process can be isolated by any conventional technologies in the art, such as HPLC, and further extracted or crystallized.

III. Process for Isolating Pravastatin without Using Chromatography

The inventors developed an improved process of isolating a (HMG)-CoA reductase inhibitor in a good yield and purity without using a chromatography and proceeding a lactonization reaction.

Accordingly, one object of the invention is to provide a process of isolating a (HMG)-CoA reductase inhibitor which comprises the steps of (1) adding an ammonium sulfate into a first solution containing the(HMG)-CoA reductase inhibitor to produce a precipitation; (2) isolating the precipitation; (3) dissolving the precipitation with a polar solvent to produce a second solution; (4) adjusting the pH of the second solution to about pH 4 to about PH 6; and (5) extracting the second solution with an water immiscible solvent to isolate the (HMG)-CoA reductase inhibitor.

In a preferred embodiment of the invention, the (HMG)-CoA reductase inhibitors is selected from pravastatin, compactin and lovastatin, and more preferably pravastatin.

The first solution of Step (1) of the present isolation process can be any solution containing a (HMG)-CoA reductase inhibitor to be isolated. In a preferred embodiment of the invention, the first solution of Step (1) of the present isolation process is a microbial fermentation broth which can be derived from any microorganism capable of producing the (HMG)-CoA reductase inhibitor. The microorganism is preferably selected from *Streptomyces roseochrornogenus* (U.S. Pat. No. 4,346,277), Actinomadura sp. (Peng, M. et al. supra and Peng Y. and A. L. Demain, supra). Aspergillus, Monascus, Penicillium, Paecilomyces, Hypomyces, Phoma, Pleurotus, Doratmyces, Eupenicillium, Gymnoaxus, Trichoderma (EP 0 877 089 A1), more preferably YS-44442 and YS-45494 of the invention, and their mutants described herein.

The ammonium sulfate of Step (1) is preferably added into the first solution in an amount of 30 to 60% (w/v) of the first solution. More preferably, the ammonium sulfate is added to be saturated in the first solution.

In Step (1) of the present isolation process, the precipitation can be isolated by any method known in this art, such as filtration, centrifugation or decantation, and a membrane filtration is preferred.

In a preferred embodiment of the invention, the pH of the second solution of Step (4) is adjusted with an inorganic acid, preferably HCl. Persons skilled in the art can select a proper acid according to conventional technologies and knowledge to adjust the pH of the second solution.

In Step (5) of the present isolation process, the technology used to extract the second solution with an water immiscible solvent is well known in this art. Persons skilled in the art can select and use a proper water immiscible solvent to successfully extract the (HMG)-CoA reductase inhibitor from the second solution. Preferably, the water immiscible solvent is an organic solvent which can be selected from ethyl acetate, acetone, toluene, dicholoromethane and isopropyl acetate, and more preferably ethyl acetate. The amount of the organic solvent to be added is dependent on the concentration of the (HMG)-CoA reductase inhibitor contained in the second solution. The time period of extraction is preferably more than 5 minutes, most preferably 5 to 30 minutes.

After extraction with an organic solvent, the organic solvent layer is collected, and then dried and de-colorized using the conventional technologies (such as anhydrous magnesium sulfate and activated carbon) to obtain an isolated (HMG)-CoA reductase inhibitor.

In one embodiment of the invention, the present isolation process further comprises a step of reacting the isolated (HMG)-CoA reductase inhibitor with an organic or inorganic cation source, preferably sodium, to generate a salt form of the inhibitor. The sodium source is preferably selected from NaOH, $Na_2CO_3$, sodium acetate (anhydrous) and sodium-2-ethyl hexanoate. The amount of cation source added and the reaction duration is dependent of the concentration of the (HMG)-CoA reductase inhibitor. Persons skilled in the art can select a proper species and amount of the cation source to obtain the salt form of the inhibitor. Preferably the cation source is added in an concentration of 0.2 to 5.0 M with stirring for 0.5 to 2.0 hours.

Without any intention to limit it in any manner, the present invention will be further illustrated by the following examples.

EXAMPLES

Example 1

A. Isolation of Strains YS-44442 and YS-45494 from Soil Samples

Soil samples used for the isolation of actinomycetes were collected from random sites. The soil samples were kept at room temperature until they dried to constant weight. One gram of an air-dried soil sample was suspended in 10 ml of sterile 5 mM phosphate buffer (pH 7.0) and stirred for 1 min in a super mixer. To germinate actinomycetes spores, the suspension of the soil sample was heated at 35° C. to 50° C. for 10 min in a shaking incubator. After a 10-fold serial dilution, the suspension was spread on agar plates containing suitable isolation medium. Colonies occurring on the plates were counted with naked eyes and examined under a light microscope for the morphological characteristic of actinomycetes. 400 strains showing positive morphological characteristics were selected from 3000 unidentified colonies. Due to a high conversion efficiency (>50%) from compactin to pravastatin and low epi-pravastatin content (<10%), strains YS-44442 and YS-45494 were selected among the 400 positive strains. The isolation conditions of YS-44442 and YS-45494 are described in Table 1.

TABLE 1

Isolation conditions of strains YS-44442 and YS-45494

| strain no. | YS-44442 | | YS-45494 | |
|---|---|---|---|---|
| Soil source | Taipei, Taiwan | | Australian desert | |
| Soil pH | 5.4 | | 9.6 | |
| pretreatment | moist heat at 50° C. for 10 min | | moist heat at 40° C. for 10 min | |
| Selective antibiotics | Nystatin | 50 µg/ml | Nystatin | 50 µg/ml |
| | Cycloheximide | 50 µg/ml | Cycloheximide | 50 µg/ml |
| | Pen G | 1 µg/ml | Gentamycin | 1 µg/ml |
| | Polymyxin B | 5 µg/ml | | |

B. Characteristics of Strains YS-44442 and YS-45494

Strain YS-44442 or YS-45494 was maintained on slants of yeast extract-malt extract agar (ISP-2) [Shirling, E. B. and Gottlieb, D., *International Journal of Systematic Bacteriology*, 16(3): 313–340 (1966)] and grew at 27° C. Inoculum for physiological tests and preparation of biomass for DNA extraction were prepared by growing in tryptone-yeast extract broth (ISP-1) [Shirling and Gottlieb supra].

(1) Morphology and Pigment Production

Morphology characterizations were performed as described by Shirling & Gottlieb supra. Culture morphology was examined by light microscopy using a Nikon Optiphot-2 microscope equipped with 45× and 100× super-long working distance objectives. Color determination of the aerial mycelium was made by observation of the mature, sporulating aerial surface growth. Color determination of the substrate mycelium and diffusible soluble pigments, other than melanins, was made by observation of the reverse side. Substrate mycelium coloration was assigned to one of the following color groups: (1) yellow-brown; (2) yellow-brown+red (or orange); (3) yellow-brown+blue (or violet); (3) yellow-brown+green. Pigment and color determinations were defined based on comparison to the Tektronix© RGB color sampler (Xerox, Inc.). Morphological characterizations were carried out on yeast extract-malt extract agar (ISP-2), oatmeal agar (ISP-3), inorganic salts-starch agar (ISP-4), and glycerol-asparagine agar (ISP-5) [Shirling and Gottlieb supra].

With respect to the results of YS-44442, on ISP-2 and ISP-4, short, flexuous (open) hooked or (short) spiraled chains of 5 to 10 spores were observed. The spores were smooth and spherical and were appropriately 2 to 3 times the hyphal diameter. Pseudosporangia were present on ISP-2 and ISP-4 but were more abundant on ISP-4. Aerial mass coloration was white (R100 G100 B100) on ISP-2 and ISP-3. No aerial mycelia were produced on either ISP-4 or ISP-5 (see Table 2). In addition, the coloration of the substrate mycelium of YS-44442 was brown (R85 G70 B40, color 2) on ISP-2, ISP-3 and ISP-4, and yellow-brown (R100 G100 B70, color 1) on ISP-5 (see Table 2). Pigments did not change in response to pH changes following addition of approximately 100 µl of 0.05 N NaOH and 0.05 N HCl. Furthermore, no soluble pigments were produced by YS-44442 (see Table 2).

As to the result of YS-45494, aerial mass coloration of the aerial mycelium was white (R100 G100 B100) on ISP 2, 3, 4, and 5. On ISP-2, the aerial mycelium was long, straight, and branched. On ISP-3, the aerial mycelium coalesced with some swelling evident at the tips of the hyphal vegetative growth. Upon aging, strain A5 fragmented into coccovassilary elements on ISP-5. The coloration of substrate mycelium was orange-brown (R100 G85 B40, group 2) on ISP-2, red-brown (R70 G55 B40, group 2) on ISP-3, light yellow-brown (R100 G100 B85, color group 1) on ISP-4, and light yellow-brown (R100 G100 B70, group 1) on ISP-5 (see Table 2). Pigments did not change in response to pH changes following addition of approximately 100 µl of 0.05 N NaOH and 0.05 N HCl. In addition, soluble pigments were observed on ISP-3 and ISP-5. Coloration was brown (R70 G55 B40) on ISP-3 and yellow (R100 G100 B85) on ISP-5 (see Table 2). Neither soluble colors changed in response to pH changes following addition of approximately 100 µl of 0.05 N NaOH and 0.05 N HCl.

The morphological characteristics observed of YS-44442 and YS-45494 are summarized in Table 2.

TABLE 2

Colony morphology of strains YS-44442 and YS-45494

| YS-44442 | | | |
|---|---|---|---|
| 2 | White | Brown (group 2) | None |
| 3 | White | Brown (group 2) | None |
| 4 | None | Brown (group 2) | None |
| 5 | None | yellow-brown (group 1) | None |

| YS-45494 | | | |
|---|---|---|---|
| ISP Medium | Aerial mass color | Substrate mycelium color | Soluble colors |
| 2 | White | Orange-brown (group 2) | None |
| 3 | White | Red-brown (group 2) | Brown |
| 4 | White | Light yellow-brown (group 1) | None |
| 5 | White | Light yellow-brown (group 1) | Yellow |

(2) Physiological Tests

Melanin production and sole carbon source utilization were determined as described by Shirling & Gottlieb supra. Melanin production was evaluated on peptone-yeast extract iron agar (ISP-6) and tyrosine agar (ISP-7) [Shirling & Goffllieb supra]. Sole carbon source utilization was evaluated on basal mineral salts agar (ISP-9) amended with the following to 1% (w/v) concentration: D-glucose (positive control), i-arabinose, sucrose, D-xylose, i-inositol, D-mannitol, D-fructose, rhamnose, raffinose, and cellulose [Shirling & Gottlieb supra]. The negative control consisted of un-amended basal mineral salts agar. Results were scored as described by Shirling & Gottlieb [Shirling & Gottlieb supra].

The results of the general growth characteristics of YS-44442 and YS-45494 are given in Table 3.

TABLE 3

General growth characteristics of YS-44442 and YS-45494

| Strain ISP medium | YS-44442 Growth | YS-45494 Growth |
| --- | --- | --- |
| 2 | Moderate | Moderate |
| 3 | Moderate | Moderate |
| 4 | Fair | Fair |
| 5 | Fair | Fair |
| 6 | Fair | Fair |
| 7 | Fair | Fair |

With respect to the carbohydrate utilization patterns of YS-44442, strongly positive utilization was observed on L-arabinose, sucrose, D-fructose, d-fructose and rhamnose. Doubtful utilization was observed on cellulose and negative utilization was observed on I-inositol and raffinose. No melanoid pigments were produced by the culture.

As to the carbohydrate utilization patterns of YS-45494, strongly positive utilization was observed on L-arabinose, sucrose, and D-fructose. Positive utilization was observed on rhamnose and raffinose. Doubtful utilization was observed on D-xylose, I-inositol, D-mannitol, and cellulose. No melanoid pigments were produced by the culture.

The results of the carbohydrate utilization patterns of YS-44442 and YS-45494 are given in Table 4.

TABLE 4

Carbohydrate utilization patterns

| | Strain | | | | | |
| --- | --- | --- | --- | --- | --- | --- |
| | YS-44442 | | | YS-45494 | | |
| | Day | | | | | |
| | 10 | 13 | 16 | 10 | 13 | 16 |
| none | − | − | − | − | − | − |
| D-glucose | ++ | ++ | ++ | ++ | ++ | ++ |
| T-arabinose | ++ | ++ | ++ | + | + | ++ |
| sucrose | ++ | ++ | ++ | ++ | ++ | ++ |
| D-xylose | ++ | ++ | ++ | − | +/− | +/− |
| i-inositol | − | − | − | +/− | +/− | +/− |
| D-mannitol | ++ | ++ | ++ | +/− | +/− | +/− |
| D-fructose | ++ | ++ | ++ | + | + | ++ |
| rhamnose | ++ | ++ | ++ | + | + | + |
| raffinose | − | − | − | + | + | + |
| cellulose | − | − | +/− | +/− | +/− | +/− |

++ = strongly positive utilization
+ = positive utilization
+/− = utilization doubtful
− = utilization negative (3) 16s rDNA Sequence Determination DNA Extraction Biomass for DNA extraction was prepared by growing in 50 ml of tryptone-yeast extract broth (ISP-1) for 10 days, with continuous shaking at 250 rpm on an orbital shaker (1-inch throw), at 27° C. [Shirling & Gottlieb supra]. The liquid culture was harvested by centrifugation for 15 minutes at 15,000×g. The biomass was transferred to a sterile mortar and pestle, and gently ground into a paste. Approximately 0.4 ml of TE buffer (10 mM tris: 1 mM ethylene-dinitrolotetraacetic acid) was added and the buffer and cell debris were transferred to a sterile 2-ml centrifuge tube with 100 µl of 10% SDS (sodium dodecyl sulfate) solution. The mixture was incubated in a water bath at 65° C. for 15 minutes. Approximately 0.5 ml of buffered phenol (pH 8) [Ausubel, F. M., Short protocols in molecular biology, 3rd ed (1995), New York, Wiley. I v. (various pagings)] was added to the tube and mixed for 10 minutes. The mixture was centrifuged at 14,474×g for 15 minutes. The aqueous layer was transferred to a sterile 2-ml centrifuge tube and 0.5 ml of chloroform-isoamyl alcohol (24:1) was added. The mixture was centrifuged at 14,474×g for 15 minutes and the aqueous layer was transferred to a sterile 2-ml centrifuge tube. Approximately 50 µl of 5 M NaCl and 1 ml of cold 95% ethanol were added to the tube, and the DNA was precipitated by holding the mixture −20° C. for 24 hours. The mixture was centrifuged at 14,474×g, for 30 minutes at 4° C., and the supernatant removed. Approximately 100 µl of 80% ethanol was added to the tube followed by centrifugation at 14,474×g for 10 minutes. The ethanol was removed and the pellet was dried for 30 minutes and re-suspended in 50 µl of sterile deionized water (18 Mohm). The DNA was stored at −20° C. until ready for use.

16s rDNA Sequence Determination

PCR amplification of the 16s rDNA sequence was performed on the extracted DNA using GibcoBRL® native Taq polymerase on a Perkin-Elmer GeneAmp® PCR System 2400. Purification of the amplified 16s rDNA was accomplished with the Bio-Rad Prep-A-Gene® DNA Purification System. Fluorescent labeled DNA for sequencing was prepared using the ABI Prism® BigDye™ Terminator Cycle Sequencing Ready Reaction Kit. DNA sequence was done on an ABI Prism® 310 Genetic Analyzer equipped with a 61 cm×50 µm capillary using the ABI Prism® POP-6™ Performance Optimized Polymer 6 according to manufacturer's instructions. Primers GMG 1 and GMG 10 were used in 16s rDNA PCR amplification and sequencing (see Table 5). The 16s rDNA PCR amplification program is as follows: (1) 94° C. for 7 minutes; (2) 94° C. for 1 minute; (3) 53° C. for 1 minute; (4) 72° C. for 2 minutes; (5) 72° C. for 6 minutes; steps 2 to 5 were repeated for 30 cycles; and (6) Hold at 4° C.

TABLE 5

Primers used in 16s rDNA PCR amplification and sequence

| Primer | Direction | Sequence (5' ⇒ 3') | |
|---|---|---|---|
| GMG 1 | 27 Forward | GAG TTT GAT CCT GGC TCA G | (SEQ ID NO: 3) |
| GMG 2 | 1385 Reverse | CGG TGT GTR CAA GGC CC | (SEQ ID NO: 4) |
| GMG 3 | 1114 Forward | GCA ACG AGC GCA ACC C | (SEQ ID NO: 5) |
| GMG 4 | 907 Reverse | CCG TCA ATT CAT TTG AGT TT | (SEQ ID NO: 6) |
| GMG 5 | 803 Forward | ATT AGA TAC CCT GGT AG | (SEQ ID NO: 7) |
| GMG 6 | 536 Forward | CAG CMG CCG CGG TAA TWC | (SEQ ID NO: 8) |
| GMG 7 | 519 Reverse | GWA TTA CCG CGG CKG CTG | (SEQ ID NO: 9) |
| GMG 8 | 357 Forward | TAG GGG AGG CAG CAG | (SEQ ID NO: 10) |
| GMG 9 | 343 Reverse | CTG CTG CCT CCC GTA | (SEQ ID NO: 12) |
| GMG 10 | 1525 Reverse | AGA AAG GAG GTG ATC CAG CC | (SEQ ID NO: 13) |

The 16s rDNA sequences of YS-44442 and YS-45494 comprise the sequences as shown in SEQ ID NO: 1 and 2, respectively. The sequences were aligned against the multiple sequence alignment dataset in the Ribosomal Database Project (RDP) [Maidak, B. L. et al., *Nucleic Acids Res.*, 28: 173–174 (2000)] using the ARB sequence editor (release 8.1). Comparisons of the 16s rDNA sequences of YS-44442 and YS-45494 to the RDP [Maidak, B. L. el al., supra] shows 99.1% and 99.0% sequence similarity, respectively, to Saccharothrix sp. NRRL B-16133 [Labeda, D. P. and R. M. Kroppenstedt, *Int. J. Syst. Evol. Microbiol.*, 50 Pt 1: 331–6 (2000)]. (http://www.eme.msu.edu/RDP/html/index.html). In addition, 16s rDNA phylogenetic distance tree, comparing YS-44442 and YS-45494 with related actinomycetes (Table 6), generated with the ARB software package (denoted as tree 0.1) is shown in FIG. 1.

TABLE 6

Actinomycetes related to strains YS-44442 and YS-45494

| GenBank Accession | Organism | Tree Designation |
|---|---|---|
| U48842 | *Nonomuraea Africana* | Nm. african |
| AB006156 | *Sebekia benihana* strain IFO 14309 | AB006156 |
| U48977 | *Nonomuraea polychroma* | Nm. plychrm |
| U48975 | *Nonomuraea helvata* | Nm. helvata |
| U28978 | *Nonomuraea pusilla* | Nm. pusill2 |
| U48843 | *Nonomuraea angiospora* | Nm. angiosp |
| X97892 | *Nonomuraea salmonea* | Nm. salmone |
| AB006158 | *Cathayosporangium alboflavum* strain IFO 16009 | AB006158 |
| U48999 | *Streptosporangium vulgare* | Sts. vulgar |
| X99942 | *Streptomyces vellosus* | X99942 |
| X60514 | *Streptomyces coelicolor* | Stm. cocli3 |
| X79853 | *Streptomyces hygroscopicus* | Stm. hyscop |
| D85121 | *Streptomyces virginiae* strain ATCC 13161 | Stm. virgi5 |
| Y15502 | *Streptomyces griseus* | Y15502 |
| X53194 | *Saccharopolyspora rectivirgula* | Scp. rectiv |
| X53198 | *Saccharopolyspora erythraea* | Scp. erythr |
| AF154128 | *Saccharopolyspora flava* | AF154128 |
| AF002818 | *Saccharopolyspora spinosa* | Scp. spinos |
| AB020031 | *Saccharothrix tangerinus* strain MK27-91F2 | AB020031 |

TABLE 6-continued

Actinomycetes related to strains YS-44442 and YS-45494

| GenBank Accession | Organism | Tree Designation |
|---|---|---|
| AF114804 | *Saccharothrix aerocolonigenes* | AF114804 |
| AF114815 | *Saccharothrix texasensis* strain NRRL B-16107T | AF114815 |
| AF114807 | *Saccharothrix espanaensis* | AF114807 |
| X76966 | *Saccharothrix mutabilis* ssp. mutabilis DSM 43853 | Sct. mutabm |
| X76965 | *Saccharothrix mutabilis* ssp. capreolus DSM 40225 | Sct. mutabc |
| M29282 | *Saccharothrix australiensis* | Sct. austra |
| AF114803 | *Saccharothrix australiensis* | Sct. austr2 |
| AF114812 | *Saccharothrix syringae* | AF114812 |
| AF114805 | *Saccharothrix coeruleofusca* | AF114805 |

C. Comparison of YS-44442 and YS-45494 with Known Microorganisms

YS-44442 and YS-45494 both exhibit phenotypic characteristics similar to those described by Bergey's Manual of Systematic Bacteriology [Cross, T., supra] for *Saccharothrix aerocolonigenes* and *Saccharothrix australiensis*, and those described by Labeda and Lyons [Labeda, D. P. and Lyons, A. J., *International Journal of Systematic Bacteriology*, 39(3): 344–358 (19689)] for *Saccharothrix texasensis* (Table 7). YS-44442 and YS-45494 differ in morphology and carbohydrate utilization patterns from published descriptions (Table 8). They also differ in carbohydrate utilization patterns with *Saccharothrix aerocolonigenes*, *Saccharothrix australiensis*, and *Saccharothrix texasensis*, (Table 8).

TABLE 7

Comparison of YS-44442 and YS-45494 to the descriptions of related microorganisms described in Cross, *T. supra* and Labeda and Lyons supra

| | | *Saccharothrix aerocolonigenes* | *Saccharothrix australiensis* | *Saccharothrix texasensis* | YS-44442 | YS-45494 |
|---|---|---|---|---|---|---|
| Aerial Mycelium | Color | white | white to yellowish-gray | white | white | white |
| | Morphology | fragmented | fragmented into coccoid elements | no description | no description | fragmented into cocco-vassilary elements |
| Spore cham | Morphology | no description | no description | no description | short theyous hooked or spiral spore chains | no description |
| | Number | no description | no description | no description | 5–10 spores cham | no description |
| Spores | Morphology* | no description | no description | no description | smooth and spherical and 2–3X the hyphal diameter | no description |
| Substrate Mycelium | Color | yellowish to brownish | brownish to yellowish-gray | dark yellow to brownish yellow | brown to yellow-brown depending on the growth medium | orange-brown, red-brown or light yellow-brown depending on the growth medium |
| | Morphology | branched | fragmented into coccoid elements | no description | presence of Pseudosporangia | some swelling at the tips of the hyphal vegetative growth |
| Soluble pigment | Color | yellowish to brownish | brownish | brown to reddish brown | none | brown or yellow depending on the growth media |

*as viewed by light microscopy

TABLE 8

Comparison of YS-44442 and YS-45494 to the carbohydrate utilization pattern of related microorganisms described in Cross, *T. supra* and Labeda and Lyons supra

| Utilization of carbon compounds | *Saccharothrix aerocolonigenes* | *Saccharothrix australiensis* | *Saccharothrix texasensis* | Strain YS-45494 | Strain YS-44442 |
|---|---|---|---|---|---|
| no carbon control | − | − | − | − | − |
| D-glucose | + | + | + | + | + |
| L-arabinose | + | − | + | + | + |
| sucrose | + | − | + | + | + |
| D-xylose | + | − | + | − | + |
| I-inositol | − | − | + | − | − |
| D-mannitol | no information | no information | no information | − | + |
| D-fructose | + | + | variable | + | + |
| Rhamnose | − | − | + | + | + |
| Raffinose | − | − | − | + | − |
| Cellulose | − | − | no information | − | − |

Based on the combined results of phylogenetic and physiological analyses, we believe strains YS-44442 and YS-45494 are distinct from one another and from the type strains of *Saccharothrix aerocolonigenes, Saceharothrix australiensis*, and *Saccharothrix texasensis* and are novel species of the genus Saccharothrix. The two strains were deposited with the China Center for Type Culture Collection (CCTCC) and given the accession number of M202001 and M202002, respectively, on Jan. 7, 2002.

Example 2
Production of Pravastatin by YS-44442 and YS-45494
(1) Preparation of Compactin Solution to be Added in a Fermentation Broth 0.3 N NaOH solution (500 ml) was warmed and kept at 50 to 60° C. The NaOH solution was added with 40 g compactin and mixed for 2 to 3 hours at 50 to 60° C. The compactin solution in NaOH was cooled down to room temperature and the pH was adjusted to 7.5 with 1N HCl. The volume of the compactin solution in NaOH was adjusted to 1000 ml and centrifuged at 1000 rpm for 20 minutes. The supernatant was sterile by filtration.

(2) Production of Pravastatin Using YS-44442 and YS-45494

1 ml of a spore suspension of YS-44442 (or YS-45494) stored in GL(10% glycerol, 5% lactose) at −80° C. was opened in laminar flower and added into a 300 ml shake flask containing 20 ml of the seed medium (for every liter: glucose 10 g, peptone 2 g, soy protein 4 g and $KH_2PO_4$ 1 g, pH 7.0±0.2). The seed culture was incubated at 27° C. for 24 to 48 hrs in a rotary shaker at 200 to 220 rpm (growth phase). Afterward, 1.5 to 2 ml of the seed culture was incubated into a 300 ml shake flask containing 20 ml of the fermentation medium (per liter: glucose 15 g, peptone 5 g, corn steep powder (C.S.P.) 5 g and soybean meal 4 g, $KH_2PO_4$ 1 g, pH 7.0±0.2). The shake flask was incubated at 27±0.5° C. for 18 to 24 hrs in a rotary shaker at 200 rpm (growth phase). The fermentation broth was added with compactin prepared as above into the fermentation broth at a final concentration of 1500 to 2000 mg/L and the incubation was continued for 16 to 24 hrs.

(3) HPLC Analysis of Pravastatin and Compactin

The fermentation broth (0.2 ml) was added into 1.8 ml deionized water. The mixture was mixed for 1 minute and centrifuged at 3000 rpm for 10 minutes. The supernatant was analyzed by HPLC using the following conditions.

| Column: | Nuclosil$_5$ C$_{18}$, 5 um(4.6 * 150 mm) |
|---|---|
| Mobile phase: | A:0.1% ($H_3PO_4$/$CH_3CN$/$CH_3OH$ = 60/32/22) |
| (*gradient) | B:$CH_3CN$ |
| Inject volume: | 10 μl |
| Flow rate: | 1.0 ml/min |
| Detection: | 240 nm |
| Retention time: | Epi-pravastatin (pravastatin epimer): 6.25 min |
| | pravastatin: 6.85 min |
| | compactin: 9.85 min |

*The mobile phase was flew with the following gradient:

| Time(min) | Flow | % A | % B |
|---|---|---|---|
| 0 | 1.0 | 100 | 0 |
| 1.0 | 1.0 | 100 | 0 |
| 1.1 | 1.0 | 30 | 70 |
| 3.5 | 1.0 | 30 | 70 |
| 3.6 | 1.0 | 100 | 0 |
| 30 | 1.0 | 100 | 0 |
| 31 | 0.0 | 100 | 0 |

(4) Calculation and Results

A standard pravastatin or compactin preparation dissolved in alkaline methanol (100% methanol and 0.1 N NaOH) and diluted with $H_2O$ were prepared. Pravastatin yield, molar conversion efficiency (ME %) and epi-pravastatin ratio (Epi %) are calculated by Formula (I), (II) and (III) as stated above.

The conversion efficiency of compactin to pravastatin, the pravastatin yield and the epi-pravastatin ratio of YS-44442 and YS-45494 are shown in Table 8.

TABLE 8

Results of Pravastatin production by strains YS-44442 and YS-45494

| Strain | Pravastatin yield | conversion efficiency | Epi-pravastatin ratio |
|---|---|---|---|
| YS-44442 | 1.0 to 1.2 g/L | 70 to 75% | 6.5 to 8% |
| YS-45494 | 1.0 to 1.5 g/L | 48 to 50% | 1.8 to 3.0% |

Example 3
Production of Pravastatin by YS-44442 and YS-45494 with Continuous Feeding of Compactin Compactin solution to be added in a fermentation broth was prepared as described in Example 1. A spore suspension of YS-44442 or YS-45494 (9 ml) stored in GL (10% glycerol, 5% lactose) at −80° C. was opened in laminar flower and added into a 3 L shake flask containing 600 ml of the seed medium as described in Example 1. The seed culture was incubated at 27° C. for 24 to 48 hrs in a rotary shaker at 200 to 220 rpm (growth phase). Afterward, 1.6 L of the seed culture was incubated into a 30 L fermentor containing 16 L fermentation medium as described in Example 1 in which 0.1 ml antifoam (LG-109) per liter was further added. The fermentation was conducted at 27° C. with an agitation at 100 to 150 rpm and an air supply of 0.9 volume air per volume broth per minute for 24 to 48 hrs. Afterward, compactin (50 to 60 g/L) was fed into the fermentation broth in an amount of 10 to 30 ml/hr. After 2 to 3 days of feeding, the fermentation was finished. The fermentation broth was analysis by HPLC as described in Example 1, and the conversion efficiency of compactin to pravastatin, the pravastatin yield and the epi-pravastatin ratio of YS-44442 and YS-45494 are calculated as stated in Example 1 and shown in Table 9.

TABLE 9

Results of Pravastatin production by YS-44442 and YS-45494 with continuous feeding of compactin

| Strain | Pravastatin yield | conversion efficiency | Epi-pravastatin ratio |
|---|---|---|---|
| YS-44442 | 1.0 to 1.5 g/L | 70 to 75% | 6.5 to 8% |
| YS-45494 | 1.0 to 1.5 g/L | 48 to 50% | 1.8 to 3.0% |

In comparison with the known microorganisms (e.g., Actinomadura sp. as described in Peng, M. et al., J. Antibiotics, supra and Peng Y. and A. L. Demain, supra) which need a conversion period of 5 to 7 days (after compactin addition) to produce a yield of 0.326 to 0.821 g/L of pravastatin with a compactin feeding concentration of 0.5 to 1.1 g/L, YS-44442 and YS-45494 of the invention are capable of producing a yield of 1.0 to 1.5 g/L of pravastatin within 24 hours (after compactin addition) with a compactin feeding concentration of 1.5 to 2.0 g/L. In addition, compactin can soon be added into a fermentation broth of YS-44442 or YS-45494 after the fermentation broth is cultured for only 18 hours (from inoculation with a seed culture). In the prior art, compactin cannot be added into a fermentation broth of Actinomadura sp. (Peng, M. et al., J. Antibiotics, supra and Peng Y. and A. L. Demain, supra) unless the broth is cultured for more than 2 days (from inoculation with a seed culture). Further, the pravastatin produced by YS-44442 or YS-45494 contains low ratio of epi-pravastatin (i.e., 6α-hydroxylation form of compactin)

which does not have a desired therapeutic efficacy and even has a negative effect in clinical therapies. The two novel microorganisms of the invention exhibit a higher tolerance to compactin and a better conversion efficiency of compactin to pravastatin.

Example 4
NTG Mutagenesis

A spore suspension of YS-44442 or YS-45494 was added into 10 ml of ISP2 medium and incubated with shaking for 1 to 2 hours. After centrifugation, the spore pellet was washed with 0.9% NaCl twice and suspended in 3 ml of 0.9% NaCl. 2.5 ml of 0.2 M NaOH and 1 ml of 1000 ppm NTG were added into the spore suspension, mixed well and incubated at 27±1° C. for 10, 20, 30, 60 and 120 min. After incubation, the spore suspension was added with 12% sodium thiosulfate and the up-layer after centrifugation was removed to eliminate the NTG. 10 ml of ISP2 medium was added into the spore suspension and incubated with shaking for 1 to 2 hours. After centrifugation, the spore pellet was washed with 0.9% NaCl twice and suspended in 0.3 ml of 0.9% NaCl. After a 10-fold serial dilution, 0.1 ml of the diluted spore suspension was spread onto ISP2 agar plates. After incubating at 27±1° C. for 6 to 9 days, morphologies and the numbers of the colonies appearing on the plates were observed and counted, respectively. Preferably, the killing rate determined by the following formula was between 50 to 99.5%.

Killing rate=(numbers of cells without NTG treatment−numbers of cells through NTG treatment)/numbers of cells without NTG treatment×100%

For example, if the agar plate spread by $10^4$ fold diluted spore suspension through NTG treatment appears 28 colonies (equivalent to $2.8 \times 10^6$ cells) and the agar plate spread by $10^6$ fold diluted spore suspension without NTG treatment appears 36 colonies (equivalent to $3.6 \times 10^8$ cells), then the killing rate is about 99.22% [100%×(360,000,000−2,800,000)/360,000,000]. Other mutagenesis using another mutagen can be conducted by the above method.

UV Irradiation Mutagenesis

A spore suspension of YS-44442 or YS-45494 was diluted by 10 fold serial dilution. 0.1 ml of diluted spore suspension was spread onto ISP2 agar plates. The agar plates were opened and treated with UV light for 30, 60, 120, 240 and 480 seconds. After UV irradiation, the agar plates were covered and immediately transferred into a black condition to avoid further light illumination. After incubating at 27±1° C. for 6 to 9 days, morphologies and numbers of the colonies appearing on the plates were observed and counted. Preferably, the killing rate determined by the following formula is between 99 to 99.999%.

Example 5
Bioactivity Assay of Mutants Derived from YS-44442 or YS-45494

After mutagenesis, the morphological variant was selected and put into screw tube with 6 to 10 glass beads and 0.5 ml deionized water, and mixed well. 0.1 to 0.15 ml of the suspension was refreshed in ISP2 slant agar and fermentated in a liquid medium. During fermentation, compactin was added in a final concentration of 1.5 or 2.1 g/L and the bioconversion was proceeded at 27° C. for 24 to 48 hours. 0.2 ml of the fermentation broth was mixed with 1.8 ml deionized water. After centrifugation, the supernatant was analyzed by HPLC as described above. Mutants derived from YS-44442 or YS-45494 were selected for their pravastatin productivity, conversion efficiency and epi-pravastatin ratio (see Table 10).

TABLE 10

Bioassay results of mutants derived from strains YS-44442 and YS-45494

| Strain | Pravastatin yield | conversion efficiency | Epi-pravastatin ratio |
| --- | --- | --- | --- |
| 44442(parent) | 1.08 g/L | 72.0% | 10.0% |
| 3600-1(mutant strain) | 1.15 g/L | 76.7% | 8.2% |
| 3600-2(mutant strain) | 1.30 g/L | 86.7% | 5.0% |
| * Compactin is fed in a final concentration of 1.5 g/L | | | |
| 45494(parent) | 1.05 g/L | 50.0% | 3.7% |
| 8400-1(mutant strain) | 1.24 g/L | 59.0% | 3.0% |
| 8400-2(mutant strain) | 1.53 g/L | 72.9% | 2.1% |
| * Compactin is fed in a final concentration of 2.1 g/L | | | |

Example 6

Purification of Pravastatin by Ammonium Sulfate Precipitation

A pravastatin-containing fermentation broth (14L, pH 7.5 to 8.5) of the mutant strain derived from the parent YS-44442 or YS-45494 was added with ammonium sulfate (4.5 to 7.0 kg) batchwise within 2 to 6 hours and then stirred for 5 to 15 hrs at room temperature to give a precipitation. The precipitation thus produced was separated by filtration. The precipitation was dissolved in 100 to 200 ml of water and stirred for 0.5 hrs to produce a solution. The solution was filtered through a bed of celite, washing the celite bed once with 100 ml of water. The filtrate was collected and the pH of the filtrate was adjusted to pH 4.0 to 6.0 with 18% (w/v) HCl. The filtrate was then mixed with 1.0 to 3.0 volume of ethyl acetate and stirred for 10 to 30 min at room temperature. The emulsion was filtered by a bed of celite. After the phases were separated, the water phase was collected and extracted again with 1.0 to 3.0 volume of ethyl acetate. The ethyl acetate phases obtained from such twice extractions were collected together. The collected ethyl acetate phases were dried and decolorized by adding with anhydrous magnesium (0.1 to 1.5% w/v) and activated carbon (0.1 to 1.5% w/v), stirring for 1 to 15 min at room temperature, filtering and washing with fresh ethyl acetate (100 ml), to yield 94.495% (HPLC) of pravastatin.

To obtain a pravastatin sodium, the pravastatin purified as above was dissolved in fresh ethyl acetate to produce a solution containing pravastatin in a concentration of 5.0 to 25.0 g/L. The solution was added with 0.2 to 5.0 M sodium-2-ethyl hexanoate in methanol/ethanol or isopropyl alcohol and stirred for 0.5 to 2.0 hrs at room temperature. The solution was then cooled to 0 to 20° C., filtered and washed with fresh ethyl acetate, yielding 60 to 80% of pravastatin with a purity of 98.5% (HPLC) wherein the single impurity is in an amount of less than 0.3% and the total impurity is less than 1.0%.

What is claimed is:

1. An isolated microorganism strain YS-44442 of Saccharothrix and the mutant thereof.

2. An isolated microorganism strain YS-45494 of Saccharothrix and the mutant thereof.

3. A process for producing pravastatin using the microorganism of claim 1 or 2.

4. The process of claim 3, comprising the steps of (a) cultivating the microorganism of claim 1 or 2 at a suitable condition to generate a fermentation broth; (b) feeding compactin into the broth; (c) fermenting the broth for a period of time to convert the compactin to pravastatin; and (d) isolating the pravastatin from the broth.

5. The process of claim 4, wherein the fermentation broth of Step (a) is cultivated for less than 2 days.

6. The process of claim 5, wherein the fermentation broth of Step (a) is cultivated for about 18 hours.

7. The process of claim 4, wherein the fermentation broth of Step (a) is derived from a seed culture of the microorganism which is cultivated at a suitable condition for about 18 to about 48 hrs before inoculation into the broth.

8. The process of claim 4, wherein the compactin of Step (b) is fed into the broth at a final concentration of higher than 1.0 g/L.

9. The process of claim 8, wherein the final concentration is about 1.5 to about 2.0 g/L.

10. The process of claim 4, wherein the period of time of Step (c) to convert the compactin to the pravastatin is less than 5 days.

11. The process of claim 10, wherein the period of time is less than 3 days.

12. The process of claim 11, wherein the period of time is less than 24 hours.

* * * * *